(12) United States Patent  (10) Patent No.: US 8,932,843 B2
Niazi  (45) Date of Patent: Jan. 13, 2015

(54) BUOYANT PROTEIN HARVESTING METHOD

(75) Inventor: Sarfaraz Niazi, Deerfield, IL (US)

(73) Assignee: Therapeutic Proteins International, LLC, Chicago, IL (US)

( * ) Notice: Subject to any disclaimer, the term of this patent is extended or adjusted under 35 U.S.C. 154(b) by 0 days.

(21) Appl. No.: 13/245,448

(22) Filed: Sep. 26, 2011

(65) Prior Publication Data

US 2012/0016113 A1 Jan. 19, 2012

(51) Int. Cl.
| C12N 1/00 | (2006.01) |
| C07K 1/14 | (2006.01) |
| B01J 20/28 | (2006.01) |
| C07K 1/16 | (2006.01) |
| C07K 1/18 | (2006.01) |
| C07K 1/20 | (2006.01) |
| C07K 1/22 | (2006.01) |
| B01D 15/22 | (2006.01) |

(52) U.S. Cl.
CPC .............. *C07K 1/14* (2013.01); *B01J 20/2805* (2013.01); *C07K 1/165* (2013.01); *C07K 1/18* (2013.01); *C07K 1/20* (2013.01); *C07K 1/22* (2013.01); *B01D 15/22* (2013.01)
USPC ...................... 435/243; 435/292.1; 435/257.1

(58) Field of Classification Search
USPC ............ 435/240.241, 383, 297.2, 289.1, 401, 435/257.1, 292.1, 243
See application file for complete search history.

(56) References Cited

U.S. PATENT DOCUMENTS

| 5,122,470 | A | * | 6/1992 | Banes ............................ 435/401 |
| 5,783,075 | A | | 7/1998 | Eddleman et al. |
| 6,544,788 | B2 | * | 4/2003 | Singh ............................ 435/383 |
| 6,610,528 | B1 | | 8/2003 | Mathur et al. |
| 7,306,934 | B2 | | 12/2007 | Arora et al. |
| 2002/0040684 | A1 | | 4/2002 | McNeil |
| 2010/0119416 | A1 | * | 5/2010 | Tajima ............................ 422/102 |
| 2012/0202274 | A1 | * | 8/2012 | Yancey, Jr. ................. 435/257.1 |

FOREIGN PATENT DOCUMENTS

WO  99/63142 A1  12/1999

OTHER PUBLICATIONS

BioPlan Associates, Inc., "Seventh Annual Report and Survey of Biopharmaceutical Manufacturing Capacity and Production," pp. 1-32 (Apr. 2010).
International Search Report and Written Opinion for corresponding PCT Patent Application No. PCT/US12/57046.

* cited by examiner

*Primary Examiner* — Sally Merkling
(74) *Attorney, Agent, or Firm* — Sarfaraz K. Niazi; Cheryl Liljestrand

(57) ABSTRACT

A buoyant device containing chromatography media performs the function of protein harvesting replacing the steps of cell separation and volume reduction; the device can be loaded into columns for further purification.

19 Claims, 1 Drawing Sheet

BUOYANT PROTEIN HARVESTING METHOD

FIELD OF THE INVENTION

The instant invention relates to a novel device and method of its use for harvesting and purifying proteins.

BACKGROUND

The present invention relates to a novel device for harvesting a recombinant protein, which device is characterized by that it comprises a container holding a chromatography media and the container if kept buoyant in nutrient media to maximize the binding of protein in nutrient media with the chromatography media; the device is then removed as harvested protein in a protein-chromatography bound stage. The protein-harvesting device can then be packed in a chromatography column in place of the customary chromatography media and purification performed as desired.

Downstream processing involves cleaning up crude proteins to yield high purity products. Traditionally, these involve use of chromatography columns and highly specialized media to capture and purify the desired proteins. With an exponential rise in the number of protein drugs being developed and marketed, there have been remarkable developments in the field of downstream processing. Still, the time and cost-consuming steps of filtration, chromatography and purification slow down the manufacturing process and add substantial capital cost requirement to establish cGMP-grade manufacturing operations. Recent surveys show that most biopharmaceutical companies consider downstream processing to be their biggest concern since the upstream processing efficiencies have improved creating an imbalance in synchronizing the processes. (7th Annual Report and Survey of Biopharmaceutical Manufacturing. BioPlan Associates, Inc; Rockville, Md.).

The improvements in the downstream processing are mostly focused on creating better chromatography medias such as Protein A or more specific antibodies and converting existing systems into disposable forms, often streamlining the various upstream and downstream processing. Given below is a summary of the art that has been developed or under development:

Single-use downstream chromatography: Novozymes's new patented Dual Affinity Polypeptide technology platform replaces Protein A process steps with similar, but disposable, technology Stimuli responsive polymers enable complexation and manipulation of proteins and allow for control of polymer and protein complex solubility, which results in the direct capture of the product without centrifuges or Protein A media, from Millipore Corp Mixed mode sorbents to replace traditional Protein A and ion exchange, for improved selectivity and capacity with shorter residence times. These media, with novel chemistries, include hydrophobic charge induction chromatography, such as MEP, and Q and S HyperCel from Pall Corp Monoliths, involving chromatography medium as a single-piece homogeneous column, such as Convective Interaction Media monolithic columns from BIA Separations Simulated moving beds, involving multicolumn countercurrent chromatography, such as BioSMB from Tarpon Biosystems Protein G (multiple vendors)

Single domain camel-derived (camelid) antibodies to IgG, such as CaptureSelect from BAC New inorganic ligands, including synthetic dyes, such as Mabsorbent A1P and A2P from Prometic Biosciences Expanded bed adsorption chromatography systems, such as the Rhobust platform from Upfront Chromatography Ultra-durable zirconia oxide-bound affinity ligand chromatography media from ZirChrom Separations Fc-receptor mimetic ligand from Tecnoge ADSEPT (ADvanced SEParation Technology) from Nysa Membrane Technologies Membrane affinity purification system from PurePharm Technologies Custom-designed peptidic ligands for affinity chromatography from Prometic Biosciences, Dyax, and others Protein A- and G-coated magnetic beads, such as from Invitrogen/Dynal New affinity purification methods based on expression of proteins or MAbs as fusion proteins with removable portion (tag) having affinity for chromatography media, such as histidine) tags licensed by Roche (Genentech)

Protein A alternatives in development, including reverse micelles (liposomes), liquid-liquid extraction systems, crystallization, immobilized metal affinity chromatography, and novel membrane chromatography systems Plug-and-play solutions with disposable components (e.g., ReadyToProcess), process development ÄKTA with design of experiments capability, and multicolumn continuous capture, from GE Healthcare.

Affinity Chromatography is a separation technique based upon molecular conformation, which frequently utilizes application specific chromatography medias. These chromatography medias have ligands attached to their surfaces, which are specific for the compounds to be separated. Most frequently, these ligands function in a fashion similar to that of antibody-antigen interactions. This "lock and key" fit between the ligand and its target compound makes it highly specific.

Lectin Chromatography. Many membrane proteins are glycoproteins and can be purified by lectin affinity chromatography. Detergent-solubilized proteins can be allowed to bind to a chromatography chromatography media that has been modified to have a covalently attached lectin.

Immunoaffinity chromatography chromatography media employs the specific binding of an antibody to the target protein to selectively purify the protein. The procedure involves immobilizing an antibody to a column material, which then selectively binds the protein, while everything else flows through.

It is surprising that most of the innovations listed above and those that form prior art involved selective interaction between a target protein and a binding material such as a chromatography media to purify the protein to the limits of pharmacopoeia which currently require a purity greater than 98% (European Pharmacopoeia) and most of manufacturers use an internal control limit of greater than 99.5% purity. However, prior to the commencement of the downstream purification process, the nutrient media needs to be treated to separate the target protein in its crude form as it is not possible to load purification columns with nutrient media without adversely affecting the separation characteristics of these columns and also without excessively prolonging the process of downstream processing that adversely affects the stability of the target protein, besides adding extremely large cost of using large columns, pumps and expensive chromatography media.

There remains a large unmet need to develop a device to capture the target protein non-selectively or selectively and remove it from the nutrient media or a refolding solution prior to subjecting it to customary purification processes. The instant invention is targeted to modify the existing methods of performing protein harvesting or protein capturing prior to purification chromatography to increase the throughput of manufacturing processing without adding expensive and technically challenging modifications.

BRIEF DESCRIPTION OF THE INVENTION

The recombinant protein manufacturing involves growing genetically modified organisms or cells in a culture media, harvesting the target protein from the rest of the contents of the nutrient media including recombinant cells or organisms and then purifying the target protein using column chromatography.

The present invention comprises a device used to contain a chromatography media that is capable of binding the proteins secreted in the nutrient media. This device is made buoyant so it will float at the surface of the nutrient media or its buoyancy modified to dispose it at different levels inside the nutrient media. The device is introduced into a bioreactor either during the bioreactor cycle or at the end of the bioreactor cycle. Once a pre-determined quantity of protein has bound to the chromatography media in the device, it is removed from bioreactor for further processing, in one instant, the device is stacked in a chromatography column and routine chromatography process conducted to purify the protein.

DETAILED DESCRIPTION OF THE INVENTION

Figure 1A:
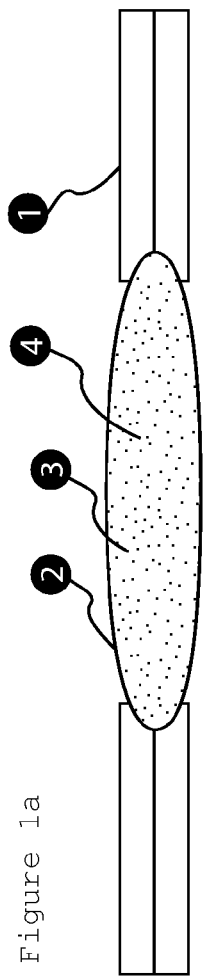
FIG. 1a is a side view of the protein-harvesting device wherein a perforated container is surrounded by a buoyant material.

FIG. 1a describes a side view of a protein-harvesting device comprising a perforated container 2, with perforations of such size 3 as to retain a chromatography media 4 inside the container. The container is surrounded by a buoyant material 1 to keep the device afloat in the nutrient media.

Figure 1B:
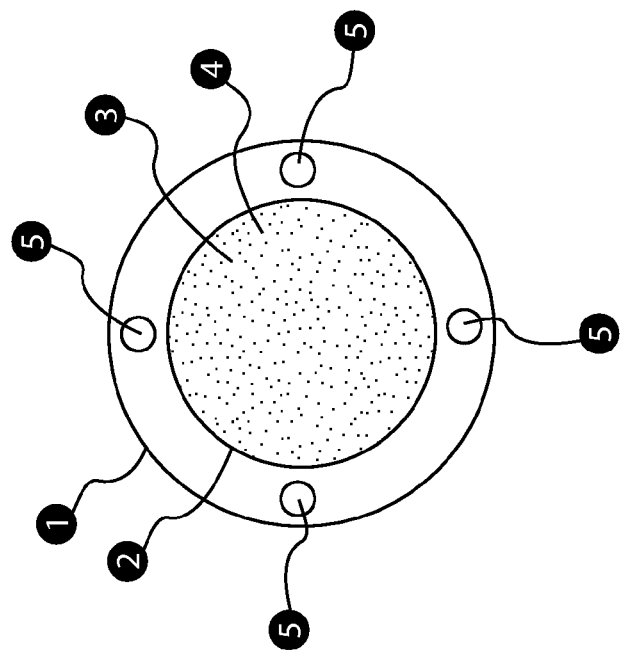
FIG. 1b is a topical view of the protein-harvesting device where a perforated container is surrounded by a buoyant material and additionally contains holes to attaché weights to change the buoyancy of the device.

FIG. 1b is a topical view of a protein-harvesting device showing how the buoyant components 1 surround the container 2 to keep it afloat; also shown in the buoyant material are holes 5 to attach weight to the buoyant material 2 to submerge it to different depths as needed.

The protein-harvesting and purification device described in the figures above is generally used at the end of the bioreactor cycle wherein a plurality of these device can be introduced in a bioreactor; the number of devices used and the amount of chromatography media contained in each device would be easily calculated by the binding efficiency of the protein. For example, Protein A chromatography media shows a binding of 30-50 mg/mL of the chromatography media. Assuming a 1,000 L nutrient media is used in a 2,000 L bioreactor and the production cycle has come to an end, a point where the CHO are no longer producing sufficient quantity of protein. Further assuming that the productivity of the recombinant cell line is about 1 G/L; thus, in this case, there is about 1000 G of protein in solution in the nutrient media that is to be removed and purified. On a theoretical basis, assuming a lower end of binding of 30 mg/mL, it will take about 33 L of chromatography media to bind substantially all of protein in the solution. It should be noted that while Protein A is rather specific to monoclonal antibodies, it is likely that the binding capacity of the chromatographic media will be compromised because of binding of other components in the nutrient media. This can be readily studied by withdrawing a small volume of the nutrient media and adding to it incremental amounts of the chromatography media used until the concentration of the protein in solution reaches to a pre-determined low value. This would be called titrating the nutrient media.

In a first embodiment, the instant invention simplifies the harvesting of proteins in a bioreactor. The instant invention employs conditions, which in one step combines several in strong contrast to common state of the art of protein separation today, and involves a process with only a fewer steps.

In particular, the present invention relates to a device used for harvesting a recombinant protein, wherein a nutrient media containing host cells and target protein are subjected to a non-specific or specific treatment with chromatography media or a combination of chromatography media contained in the device that would bind all or substantially all of charged or uncharged molecular species, this step is followed by removing the chromatography media-protein complex by simply removing the device from the bioreactor. The present invention thus obviates a major hurdle in the harvesting of proteins that involves filtering out host cells using a fine filter, not larger than 5μ, to retain host cells such as Chines Hamster Ovary Cells. When large volume of media is used, this process takes a very long time, adds substantial cost of filters, pumps, containers and space management. This step is then generally followed by a concentrating step wherein the volume of nutrient media is reduced most to one-tenth its volume using a cross-flow or micro filtration process, which takes a very long time to complete and again adds substantial cost of equipment and manpower and in some instances causes degradation of target protein. The instant invention combines these two steps into one simple step. The argument that if it is the intent to harvest and concentrate protein from a complex mixture containing host cells, why would it not be more efficient to remove the protein from the mixture instead of removing other components that are present in much larger quantities. This is what would be considered a contrarian teaching. In the instant invention, those peculiar characteristics of target proteins are exploited to separate them from the rest of the mixture by a non-specific binding to a chromatography media or a mixture of chromatography medias. Obviously, such non-specific capture of target proteins would also capture other components of the mixture and that only requires using a much larger quantity of chromatography media or a specific type of chromatography media that might have specific affinity for the target protein. The removal of protein-chromatography media complex is a much simpler process than the removal of host cells or reduction in the volume of mixture; any mechanical process such as decanting, centrifugation or even filtration would work. It is noteworthy that the slowest of all processes would be filtration but even the much larger pore size filter can be used and since the purpose is to collect the filtrate, not the eluate, the cost of manufacturing is lowered substantially.

In a second embodiment of the instant invention, it can be applied to concentration of proteins in stages other than the bioreactors. The steps of harvesting proteins are also involved in the concentration of protein after it has been refolded in a very dilute solution and whereas these solutions are of high purity and can be readily filtered, it is most frequently seen that the filtration of a refolded solution results in a substantial loss of protein due to degradation; the instant invention resolves this problem by removing all or substantially all of protein solution from the refolding solution, removing the buffers and reconstituting the protein eluted from the chromatography media-protein complex for further purification.

In a third embodiment, the instant invention can be applied to separation of any protein solution including industrial production of proteins.

In a fourth embodiment, the instant invention avoids obviates the need for costly filtration processes for every type of manufacturing of proteins as in almost all instances a concentration step is involved.

In a fifth embodiment, the instant invention provides a means of continuously removing expressed protein from a nutrient media to enhance the level of expression that may be depressed because of the higher concentration of protein in the mixture.

In a sixth embodiment, the instant invention provides a means of continuously removing expressed protein from a nutrient media to reduce the toxicity of the expressed protein to host cells and thus prolonging the cycles of expression substantially increasing the yields of production. In a biological system, a particular protein is expressed only in a specific subcellular location, tissue or cell type, during a defined time period, and at a particular quantity level. This is the spatial, temporal, and quantitative expression. Recombinant protein expression often introduces a foreign protein in a host cell and expresses the protein at levels significantly higher than the physiological level of the protein in its native host and at the time the protein is not needed. The over-expressed recombinant protein will perform certain function in the host cell if the protein is expressed soluble and functional. The function of the expressed recombinant protein is often not needed by the host cell. In fact the function of the protein may be detrimental to the proliferation and differentiation of the host cell. The observed phenotypes of the host cells are slow growth rate and low cell density. In some cases, the recombinant protein causes death of the host cell. These phenomena are described as protein toxicity. These recombinant proteins are called toxic proteins.

Protein toxicity is a commonly observed phenomenon. All active proteins will perform certain functions. The host cells need all of these functions with few exceptions and therefore they interfere with cellular proliferation and differentiation. The appeared phenotype of the effects of these proteins to the host cells is their "toxicity". It is estimated that about 80% of all soluble proteins have certain degree of toxicity to their hosts. About 10% of all proteins are highly toxic to host cells. The completely insoluble or dysfunctional proteins will not be toxic to the host cell, though they may drain the cellular energy to produce them when over-expressed. Protein over-expression creates metabolic burden for the host cell, but this burden is not toxicity to the cell. Some low solubility or partially functional proteins may still be toxic to the host. While the exposure of the host cell to protein being expressed is inevitable and is only optimized through codon usage, once the protein has been expressed, it would be prudent to transport it out of the cell as soon as possible and this diffusion reaction requires establishing a sink condition that is readily achieved if the expressed protein in the surroundings of the host cell is removed from the solution such as in the case of the instant invention by binding to a chromatography media.

In a seventh embodiment, the instant invention provides a means of increasing the chemical stability of expressed protein by binding it to a chromatography media as soon as it is expressed as the chemicals are always less stable in a solution form than in a solid form or in this case a complex form; this would substantially improve the yield of production. The very nature of the recombinant product makes it unstable. Instability of a recombinant protein can be separated into either physical instability issues or chemical instability issues. Physical instability can be related to such things as denaturation of the secondary and tertiary structure of the protein; adsorption of the protein onto interfaces or excipients; and aggregation and precipitation of the protein. In most biopharmaceutical processes, additives are used to improve the physical stability of a protein. The addition of salts can significantly decrease denaturation and aggregation by the selective binding of ions to the protein. Polyalcohols can also be used to stabilize the protein by selective solvation. Finally, surfactants are often used to prevent the adsorption of proteins at the surface, although there is a fine line between the amount of surfactant needed to prevent adsorption and the amount needed to denature a product. In addition, excipients are often used to prevent aggregation. Chemical instability of a protein product results in the formation of a new chemical entity by cleavage or by new bond formation. Examples of this type of instability would be deamidation, proteolysis and racemization. There are some more obvious choices to improve the chemical instability, such as modulation of pH, the use of low temperatures for storage and processing, and the addition of preservatives. In the process of recombinant manufacturing where proteins are secreted into media, there are two methods widely used. In one method of batch processing, the proteins are harvested at the end of the cycle that might be as long as several weeks of continuous expression; while many proteins would survive the 37 C environment for that length of time, many would degrade over period of time. By capturing the proteins through formation of chromatography media-protein complex, the stability of and thus the yield of production can be increased since in the complex stage, the molecules are immobilized and thus less likely to decompose. While many proteins may decompose by adsorbing to various surfaces, the interaction between a chromatography media and protein is of a different nature as evidenced by the use of chromatography medias in the purification of proteins whereby high degree of stability is maintained when eluting from a chromatography media column. In another situation, where a perfusion system is used for the upstream production of recombinant proteins, a portion of nutrient media is replaced with fresh media and the media removed is filtered of host cells, reduced in volume and either stored at a lower temperature or processed with downstream processing. This technique also adds substantial cost to production in media and its handling; by passing the media through a column containing the chromatography media, which can be replaced with fresh chromatography media periodically, the expressed protein can be removed readily without affecting the total count of viable host cells; while the chromatography media might also absorb some of the nutrients, these can be easily replaced in a fed-batch culture systems.

In an eight embodiment, the instant invention provides a means of substantially reducing the cost of recombinant drug manufacturing by eliminating some of the most costly and time consuming steps. The cost of using a chromatography media is minimal as this can be used repeatedly. The purification of biological therapeutics generally involves the use of cross flow filtration (tangential flow filtration), normal flow filtration (dead ended filtration) combined with chromatographic separations. Cross flow filtration and normal flow filtration retain matter through size exclusion and are complementary to chromatography's selectivity. For processes where volumes are large such as into thousands of liters, the cost of equipment for filtration is into hundreds of thousands of dollars with expensive filters all adding to a cost that represents a major fraction of the total cost of manufacturing of recombinant drugs.

In the night embodiment, the instant invention combines several steps of upstream and downstream; the chromatography media-protein complex as contained in the container of the device is ready for downstream processing that can be accomplished by loading the device onto a column; this can save substantial time for loading; this prolonged delay can also be detrimental to the stability of target protein.

In the tenth embodiment, the instant invention offers to eliminate a very laborious and expensive step of first stage filtration or other means of separating the protein harvested; by using a device to contain the chromatography media, all steps generally required to remove chromatography media such as decanting, centrifugation (low speed), filtration (coarse) can be avoided altogether; the containers can be stringed together so that these are simply removed by picking up the end of the string at one end. The claimed device can also be then packed directly in a column for elution as if this were loose chromatography media.

In the eleventh embodiment, the instant invention allows to adjust the physicochemical characteristics of the nutrient media to achieve optimal binding of proteins with chromatography media improving the yield.

In the twelfth embodiment, the instant invention allows for the use of a mixed-bed chromatography media that may contain an ionic chromatography media, a hydrophobic chromatography media and an affinity chromatography media all used together to optimize the efficiency of harvesting. It is well established that the use of ionic chromatography medias does not allow complete capture of proteins because of the logarithmic nature of ionization; a combination of chromatography medias used in the instant invention allows for a more complete recovery of target proteins. Since the purpose of reaction at the chromatography media-protein complexation stage is to harvest and not purify the protein, the calculations like chromatography plates for purification are not important and neither is the particle size o the chromatography media allowing use of the cheapest chromatography media available; any lack of efficiency in capturing proteins can be readily adjusted by increasing the quantity of chromatography media. The chromatography media can be used repeatedly after washing of the proteins and sanitizing the chromatography media.

In the thirteenth embodiment, the instant invention describes a novel method of protein purification wherein the loading of purification column is avoided; the protein-chromatography complex in the device is already loaded. Often it takes hours and days to load a column, these steps are obviated in the use of the claimed device.

In the fourteenth embodiment, the instant invention describes a method of keeping the chromatography media binding the protein separate from the nutrient media inside a bioreactor and thus allowing separation of wasted nutrient media and cells by simply draining the bioreactor; this eliminates at least three steps in downstream processing, viz., filtration of culture broth to remove cells, cross-flow filtration to reduce the volume of broth and finally loading of protein solution onto a separation column.

In the fifteenth embodiment, the instant invention describes a device capable of containing a chromatography media capable of binding the proteins and it is added in a device that is capable of floating in the nutrient media; furthermore, the buoyance of the device can be adjusted by applying various weight to it to assure that these devices are submerged in the nutrient media at different levels to maximize the binding of the protein to the chromatography media.

The embodiments described above do not in any way comprises all embodiments that are possible using the instant invention and one with ordinary skills in the art would find many more applications specific to a complex process or even in those processes where such needs might not be immediately apparent.

Prior art on using chromatography medias to harvest recombinant proteins is non-existent; the U.S. Pat. No. 7,306,934 issued on 11 Dec. 2007 to Arora et al., teaches the use of porous solid ion exchange wafer for immobilizing biomolecules, said wafer comprising a combination of an biomolecule capture-chromatography media containing a transition metal cation of +2 valence; it also teaches a separative bioreactor, comprising an anode and a cathode, a plurality of reaction chambers at least some being formed from a porous solid ion exchange wafers (above) having a combination of art biomolecule capture-chromatography media and an ion-exchange chromatography media and having a genetically engineered tagged biomolecule immobilized on said biomolecule capture chromatography media, each of said porous solid ion exchange wafers being interleaved between a cation exchange membrane and an anion exchange membrane, and mechanism for supplying an electric potential between the anode and the cathode. The instant invention is significantly different from the separative bioreactor taught by Arora. First, the instant invention does not require use of electrodes, chromatography medias with a transition cation of +2 valence or immobilized metal ion affinity chromatography. The use of EDI (electrodeionization) and specific use of tags and limited nature of solvents to remove the captured proteins mainly enzymes makes this patent teachings distinctly different from the instant invention. Moreover, the Arora patent adds a hardware that adds to the cost of processing purification of proteins while the instant invention combines several processes into one without adding any new cost element.

What I claim is:

1. A method of harvesting proteins in a bioreactor comprising:
    a. Providing the protein-harvesting device comprising a porous container with an inner volume comprising a suitable amount of a chromatography media wherein said media is capable of binding a protein; and a buoyancy device attached to the porous container;
    b. Disposing the protein-harvesting device in a container comprising a genetically modified organism or cells capable of producing a protein for harvesting in a nutrient media;
    c. Adjusting the buoyancy of the protein-harvesting device to a pre-determined level;
    d. Adjusting the pH and electrolyte concentration of the nutrient media to optimize the binding of the protein to the chromatography media;
    e. Testing the nutrient media until the concentration of the protein in the nutrient media reaches a pre-determined low value;
    f. Removing the protein-harvesting device from the nutrient media for further processing of the protein bound to the chromatography media.

2. The method of harvesting proteins according to claim 1, wherein a plurality of protein-harvesting devices is used.

3. The method of harvesting proteins according to claim 1, wherein the plurality of protein-harvesting devices is submerged to different depths in the container containing the nutrient media.

4. The method of harvesting proteins according to claim 1, wherein the plurality of protein-harvesting devices contain different chromatography media or a combination of different types of chromatography media.

5. The method of harvesting proteins according to claim 1, wherein the protein in the protein-harvesting device in step (f) is purified by:
   a. Packing a plurality of protein-harvesting devices in a vertical column comprising an opening in the top and a drain in the bottom and an inner volume;
   b. Adding a solution of such pH and electrolyte concentration as to break the binding between the protein and the chromatography media to recover a purified form of the protein.

6. The method according to claim 1, wherein the buoyancy device is comprised of a continuous thin walled plastic body enclosing a substantially hollow interior.

7. The method according to claim 1, wherein the buoyancy device is made of polymeric foam and encircling the container.

8. The method according to claim 1, wherein the buoyancy device is made of cork and encircling the container.

9. The method according to claim 1, wherein the buoyancy device is inflatable.

10. The method according to claim 9, wherein the buoyancy device is inflated to different pressures to produce buoyancy.

11. The method according to claim 1, wherein the buoyancy device additionally comprises weights to submerge it partially or completely.

12. The method according to claim 1, wherein the container of step (b) is a flexible bag.

13. The method according to claim 1, wherein the porous container of step (a) is made of nylon mesh or a flexible perforated plastic.

14. The method according to claim 1, wherein the porous container of step (a) is made of perforated plastic, wood, or metal.

15. The method according to claim 1, wherein the porous container comprises a plurality of pores having a size ranging from 5 microns to 50 microns.

16. The method according to claim 1, wherein the porous container comprises a plurality of pores having a size ranging from 50 to 100 microns.

17. The method according to claim 1, wherein the porous container comprises a plurality of pores having a size ranging from 100 to 300 microns.

18. The method according to claim 1, wherein the protein harvesting device is circular, rectangular or cuboid.

19. A method of harvesting proteins in a bioreactor comprising:
   a. Providing the protein-harvesting device comprising a porous container with an inner volume comprising a suitable amount of a chromatography media wherein said media is capable of binding a protein; and a buoyancy device attached to the porous container;
   b. Disposing the protein-harvesting device in a container comprising a genetically modified organism or cells capable of producing a protein for harvesting in a nutrient media;
   c. Adjusting the buoyancy of the protein-harvesting device to a pre-determined level;
   d. Adjusting the pH and electrolyte concentration of the nutrient media to optimize the binding of the protein to the chromatography media;
   e. Removing the protein-harvesting device from the nutrient media for further processing of the protein bound to the chromatography media.

* * * * *